United States Patent [19]

Tomko et al.

[11] Patent Number: 4,950,757

[45] Date of Patent: Aug. 21, 1990

[54] PROCESS FOR MANUFACTURE OF MELAMINE PYROPHOSPHATE

[75] Inventors: John Tomko, Dobbs Ferry; Alan M. Aaronson, Flushing Meadows, both of N.Y.

[73] Assignee: Akzo America Inc., New York, N.Y.

[21] Appl. No.: 393,164

[22] Filed: Aug. 14, 1989

[51] Int. Cl.$^5$ .................... C07D 251/70; C07F 9/48
[52] U.S. Cl. .................................................. 544/195
[58] Field of Search ...................................... 544/195

[56] References Cited

U.S. PATENT DOCUMENTS

| | | | |
|---|---|---|---|
| 3,635,970 | 1/1972 | Fessler et al. | 260/249.6 |
| 3,914,193 | 10/1975 | Fessler et al. | 260/17 R |
| 3,920,796 | 11/1975 | Sheridan | 423/313 |

*Primary Examiner*—John M. Ford
*Attorney, Agent, or Firm*—Richard P. Fennelly; Louis A. Morris

[57] ABSTRACT

Melamine pyrophosphate is made by the direction reaction of pyrophosphoric acid and melamine in an aqueous reaction medium at a temperature of from about 0° C. to about 60° C., preferably from about 0° C. to about 20° C.

10 Claims, No Drawings

PROCESS FOR MANUFACTURE OF MELAMINE PYROPHOSPHATE

BACKGROUND OF THE INVENTION

Melamine pyrophosphate [CAS Registry No. 13518-93-9]also called 1,3,5-triazine-2,4,6-triamine, pyrophosphate (2:1), is a known fire retardant additive for intumescent coatings. Certain disclosures exist in the prior art in regard to its method of manufacture.

U.S. Pat. Nos. 3,635,970 and 3,914,913 disclose mixing a pyrophosphate salt in water with melamine and a mineral acid. The mineral acid is present in sufficient amount to liberate pyrophosphoric acid from the pyrophosphate salt. The temperature of the reaction is preferably 75° C. to 85° C.

U.S. Pat. No. 3,920,796 discloses treatment of melamine phosphate in a calciner at 170° C. to 325° C. to form melamine pyrophosphate.

DESCRIPTION OF THE INVENTION

The present invention is a novel process for the manufacture of melamine pyrophosphate. It involves the direct, one step reaction of melamine and pyrophosphoric acid in aqueous media. The reaction can be run at temperatures of from about 0° C. to about 60° C., preferably at temperatures at the lower end of said range (e.g., 0° to 20° C.) so that the rate of hydrolysis of pyrophosphoric acid to orthophosphoric acid is minimized. The ratio of pyrophosphoric acid to melamine that can be used is around 1:2 on a molar basis although higher amounts of pyrophosphoric acid can be used. The Example shows reaction of an approximate equimolar amount of each reactant. An excess of pyrophosphoric acid can be used to insure complete reaction, if desired. The use of higher amounts of melamine than used in the foregoing 1:2 molar ratio will result in the presence of unreacted melamine and may not be preferred for that reason.

The product, when isolated from the reaction mixture, can be easily dried using temperatures of from about 100° to about 250° C.

It is also deemed within the contemplation of the present invention to prepare the melamine pyrophosphate by a continuous process utilizing an intensive solids/liquid mixing device for high viscosity or tacky materials (e.g., as sold under the trademark KNEADERMASTER by Patterson Kelly Inc.) cooled to the temperatures described above (e.g., about 5° C.). Into such a mixing device would be placed polyphosphoric acid in water solution at the desired concentration along with a small amount of seed crystals of pyrophosphoric acid to crystallize the liquid solution to a solid. The resulting pyrophosphoric acid can then be added, on a continuous basis, to a vigorously stirred aqueous slurry of melamine.

The instant invention is further illustrated by the Example which follows.

EXAMPLE

Ice-cold water (240 cc) and crystalline pyrophosphoric acid (36.7 grams, 0.206 mole) were placed into a 500 cc reaction flask fitted with a mechanical stirrer and an ice-water cooling bath. The mixture was stirred and cooled until the acid had dissolved. Melamine (24.7 grams, 0.195 mole) was then added with vigorous stirring at 10° C. over a two minute period. An exothermic reaction took place, and the reaction temperature rose to 13° C. The exothermic reaction subsided after about 25 minutes at which time the temperature dropped to 4° C. The resulting reaction slurry was stirred at 2° C. for an additional three hours.

The resulting white slurry was filtered and was washed three times with 25 cc of water, and the resulting white crystalline solid was dried in a vacuum oven at 75° C. for nine hours.

The weight of the dried product was 40.8 grams as compared to a theoretical weight for 0.195 mole of melamine pyrophosphate of 41.9 grams. The melamine pyrophosphate (by ion chromatography) in the final product was 80% by weight with the remaining 20% being melamine orthophosphate Elemental analysis of the product gave the following results: %C— Found: 19.51; Theory: 16.7; %H — Found: 3.86; Theory: 3.72; %N — Found: 39.08; Theory: 39.05; and %P — Found: 12.79; Theory: 14.41.

The balance of the unreacted starting pyrophosphoric acid was recovered by stripping of the aqueous filtrate. No melamine was detected in the mother liquor.

We claim:

1. A process for the manufacture of melamine pyrophosphate which comprises the reaction of pyrophosphoric acid and melamine in aqueous media.

2. A process as claimed in claim 1 wherein the ratio of pyrophosphoric acid to melamine is about 1:2 on a molar basis.

3. A process as claimed in claim 1 wherein the reaction is conducted at a temperature of from about 0° C. to about 60° C.

4. A process as claimed in claim 2 wherein the reaction is conducted at a temperature of from about 0° C. to about 60° C.

5. A process as claimed in claim 2 wherein the reaction is conducted at a temperature of from about 0° C. to about 20° C.

6. A process as claimed in claim 3 wherein the reaction is conducted at a temperature of from about 0° C. to about 20° C.

7. A process as claimed in claim 1 wherein a crystallized solid of pyrophosphoric acid is added to a stirred aqueous solution of the melamine from a solids/liquid mixing device.

8. A process as claimed in claim 7 wherein the ratio of pyrophosphoric acid to melamine is about 1:2 on a molar basis and the temperature is at or below ambient temperature.

9. A process as claimed in claim 8 wherein the temperature is from about 0° C. to about 60° C.

10. A process as claimed in claim 8 wherein the temperature is from about 0° C. to about 20° C.

* * * * *